United States Patent
Ikeda

(10) Patent No.: US 8,333,690 B2
(45) Date of Patent: Dec. 18, 2012

(54) ENDOSCOPIC FLUID FEED SYSTEM

(75) Inventor: Toshiyuki Ikeda, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 966 days.

(21) Appl. No.: 12/371,274

(22) Filed: Feb. 13, 2009

(65) Prior Publication Data

US 2009/0209822 A1 Aug. 20, 2009

(30) Foreign Application Priority Data

Feb. 15, 2008 (JP) ................................. 2008-034684

(51) Int. Cl.
*A61B 1/00* (2006.01)
*A61B 1/12* (2006.01)
(52) U.S. Cl. .......................... 600/132; 600/158; 600/159
(58) Field of Classification Search .................. 600/126, 600/132, 133, 152, 156–159
See application file for complete search history.

(56) References Cited

U.S. PATENT DOCUMENTS

| | | | | |
|---|---|---|---|---|
| 4,526,622 | A * | 7/1985 | Takamura et al. | 134/21 |
| 4,552,130 | A * | 11/1985 | Kinoshita | 600/158 |
| 4,860,731 | A * | 8/1989 | Matsuura | 600/157 |
| 7,678,044 | B2 * | 3/2010 | Fujikura | 600/115 |
| 7,914,443 | B2 * | 3/2011 | Uchimura et al. | 600/110 |
| 2002/0040181 | A1 | 4/2002 | Arai et al. | |
| 2005/0065405 | A1 * | 3/2005 | Hasegawa | 600/158 |
| 2007/0204890 | A1 | 9/2007 | Torii | |

FOREIGN PATENT DOCUMENTS

| | | |
|---|---|---|
| EP | 1832226 A1 | 9/2007 |
| JP | 2006-042874 A | 2/2006 |

OTHER PUBLICATIONS

Chinese Office Action (with English translation) in corresponding Chinese Patent Application No. 200910007421.6 dated Dec. 23, 2011.
European Search Report dated May 25, 2009 cited in corresponding EP 090001977.9 now EP 2,090,217.
Japanese Office Action dated Jul. 6, 2012 issued in corresponding Japanese Patent Application No. 2008-034684 (English translation is attached).

* cited by examiner

*Primary Examiner* — Anhtuan Nguyen
*Assistant Examiner* — Alireza Nia
(74) *Attorney, Agent, or Firm* — Birch Stewart Kolasch & Birch, LLP

(57) ABSTRACT

On a rigid tip end section at the distal end of an elongated endoscopic insertion member, an observation window washer means is provided to wash an endoscopic optical observation window, along with a fluid injection means to be used for injecting a fluid from an injection passage leading to an injection hole opened on the rigid tip end section of the insertion member. Connection ports to a wash liquid conduit and a compressed air conduit of the observation window washer means are opened at a conduit connection terminal of a multiplex connector on a proximal end of a universal connection cable. Disconnectibly connected to the conduit connection terminal is a conduit coupler member having a wash liquid conduit and a compressed air conduit to supply a wash liquid and compressed air to the wash liquid conduit and compressed air conduit on the side of the conduit connection terminal. Further, an end of a injection passage is opened in the conduit connection terminal, while an injection fluid feed line is disconnectibly connected to a connection port which is provided at a lateral side of the conduit coupler member and which is brought into communication with the injection passage when the conduit coupler member is plugged into the conduit connection terminal.

5 Claims, 6 Drawing Sheets

ENDOSCOPIC FLUID FEED SYSTEM

TECHNICAL FIELD

This invention relates to an endoscopic fluid feed system for an endoscope having an observation window washer means on a rigid tip end section at the distal end of an elongated insertion member, along with a fluid injection means for injecting other cleaning liquid or a medicinal liquid from the rigid tip end section toward an intracavitary site under observation or treatment.

TECHNICAL BACKGROUND

Usually, an illumination window or illumination windows and an optical observation window are provided on a rigid tip end section at the distal end of an endoscopic insertion member or rod. In order to wash smudged observation window, an observation window washer means is normally provided on an endoscope thereby to feed wash air and liquid for cleaning purposes. The observation window washer means is constituted by a wash fluid passage which is connectible to a jet nozzle located in the vicinity of an observation window. A wash fluid passage of this sort is passed through a universal connection cable which is extended out from a manipulating head assembly of the endoscope, to which a proximal end of an endoscopic insertion member is connected. The wash fluid passage is led out from a connector which is provided at the fore distal end of the universal connection cable. From a jet nozzle, a wash liquid is spurted out toward the observation window along with compressed air. For this purpose, the observation window washer means is provided with a liquid feed tank as a wash fluid source, and an air pump. A control valve is mounted on the manipulating head assembly of the endoscope, and the control valve is manipulated by a finger of an operator to trigger jets of wash liquid and blasts of compressed air toward the observation window.

The above-mentioned endoscopic observation window washer means constitutes an endoscopic fluid feed system, and may include a fluid injection means in some cases. In the endoscopic observation window washer means, which is intended to supply a wash liquid and/or compressed air toward surfaces of an endoscopic observation window, a wash fluid feed passage which is provided axially and internally of an endoscopic insertion member is arranged to turn a fluid flow direction substantially at right angles relative to the longitudinal axis of the insertion member on introduction into a jet nozzle. In contrast, a fluid injection means is primarily resorted to at the time of washing an intracavitary site with jets of a wash fluid. Namely, a fluid injection means is resorted to primarily for the purpose of washing away contaminants from an endoscopic observation site with jets of a wash liquid under high pressure because deposition of blood or other body fluids or solid contaminants on an intracavitary site under observation would considerably hinder visibility of an intracavitary side under observation through an endoscopic observation window on a rigid tip end section of an endoscopic insertion member. A fluid injection means is also used for injection of a coloring agent or a medicinal liquid. Thus, normally a fluid injection means is adapted to spurt a jet of liquid forward in the direction of longitudinal axis of an endoscopic insertion member.

A fluid injection means is opened in an end face of a rigid tip end section, at a terminal end of an injection passage to which a fluid feed conduit from a fluid supply source is disconnectibly connected. Therefore, an injection passage is extended internally and axially through an elongated insertion member at least as far as a manipulating head assembly of an endoscope. In some cases, both an injection passage and a fluid feed conduit are provided on a manipulating head assembly of an endoscope. In such a case, however, an external conduit which is connected to the manipulating head assembly can hinder manipulations of the endoscope. Further, there has been known an endoscope having an injection passage extended internally of a universal connection cable. In this regard, it has been known in the art to connect a fluid feed conduit disconnectibly to a connection port on a connector which is attached to a distal end of a universal connection cable for connecting the endoscope to an external light source and other external components, for example, as shown in Patent Literature 1 below.

Prior Art Patent Literature

[Patent Literature 1] Japanese Laid-Open Patent Application 2003-33320.

SUMMARY OF THE INVENTION

[Problem(s) Solved by the Invention]

It has been the general practice to incorporate an air pump of an observation window washer means into an external component unit like a light source. On the other hand, a liquid feed tank which needs refilling is set in an external position, normally fixedly supported on a casing of a light source. Generally, a wash liquid is fed from the tank by applying a pressure on the wash liquid surface instead of directly pumping out the liquid from the tank by the use of a feed pump. For this purpose, compressed air is supplied from an air pump. Thus, a liquid feed tank of an observation window washer means is connected with both wash liquid feed conduit and compressed air conduit. These wash fluid feed conduit and compressed air conduit are provided in a flexible double tube having inner and outer tubes to serve as a wash fluid feed conduit and a compressed air conduit, respectively. Further, a fluid injection passage of a fluid injection means, which is extended internally into a universal cable from a distal end of an endoscopic insertion member, is disconnectibly connected with a fluid feed conduit in a connector of the universal connection cable. In this case, the fluid feed conduit is normally constituted by a flexible tube similar to the above-mentioned flexible double tube.

In this manner, a connection port for a flexible double tube of an observation window washer is opened in a housing of a connector on a universal connection cable, along with a connection port for a fluid feed conduit of a fluid injection means. In the prior art including above-mentioned Patent Literature 1, these connection ports are provided in a housing of a connector of a universal connection cable independently of each other. That is, the flexible double tube of the observation window washer and the fluid feed conduit of the fluid injection means are separately connected to the connector.

The above-mentioned connector is provided at the distal end of a universal connection cable, so that it should be as small as possible in size. Therefore, in a case where two fluid connection ports are provided separately on one connector, the connector necessarily becomes complicated in construction. Further, when there is a necessity for using an observation window washer unit and a fluid injection unit at one time, a flexible double tube of the observation window washer as well as a fluid feed conduit of the fluid injection unit has to be connected to or disconnected from the connector in a very annoying fashion.

With the foregoing in view, it is an object of the present invention to provide an endoscopic fluid feed system for an endoscope having an endoscopic observation window washer means along with a fluid injection means, permitting to connect both of the observation window washer means and fluid injection means simultaneously to a connector on a proximal end of a universal connection cable by the use of a conduit coupler member.

It is another object of the present invention to provide an endoscopic fluid feed system having, on a connector at a proximal end of a universal connection cable, wash fluid feed portions for supply of a wash liquid and compressed air to be used for washing an endoscopic observation window, along with a feed portion for supply of an injection fluid.

It is still another object of the present invention to provide an endoscopic fluid feed system, permitting to complete fluid supply routes of an endoscopic observation window washer means and a fluid injection means simply by plugging a conduit coupler member into a conduit connection terminal on a connector at a proximal end of a universal connection cable.

[Means for Solving Problems]

According to the present invention, in order to solve the above-stated objectives, there is provided an endoscopic fluid feed system for use with an endoscope having an endoscopic optical observation window on a rigid tip end portion at a fore distal end of an elongated insertion member extended forward from a manipulating head assembly, a multiplex connector provided at a proximal end of a universal connection cable from the manipulating head assembly to disconnectibly connect the endoscope to external component units, and an observation window washer means and a fluid injection means for injecting a fluid into a body cavity from an injection passage leading to an injection hole opened on the rigid tip end section of the insertion member, characterized in that the fluid feed system comprises: a conduit connection terminal provided on the multiplex connector, providing connection ports for a wash fluid conduit and a compressed air conduit of the observation window washer means; and a conduit coupler member adapted to be disconnectibly connected to the conduit connection terminal and internally formed with a wash liquid supply conduit in communication with a liquid feed tank, and a compressed air supply conduit to be disconnectibly connected to the compressed air conduit for supply of compressed air to apply a pressure on a liquid surface in the liquid feed tank; the conduit coupler member being provided with an injection fluid connection port to the injection passage, which injection fluid connection port being disconnectibly connectible to an injection fluid supply conduit; the injection fluid connection port being communicated with the injection fluid passage when the conduit coupler member is connected to the conduit connection terminal.

In order to simplify the multiplex connector in construction, ends of wash fluid conduits in communication with a compressed air feed conduit and liquid feed conduit from the injection passage and air passage are opened in the conduit connection terminal on the multiplex connector. On the other hand, the conduit coupler member is provided with a coupler body which is adapted to be disconnectibly connected to the conduit connection terminal, the coupler body having three connecting passages for connection with a compressed air conduit, wash liquid conduit and injection passage, respectively.

In this instance, connecting ends of a wash liquid conduit and a compressed air conduit, both in communication with the liquid feed tank, are opened on a coupler body of the conduit coupler member. These conduits may be connected separately to the liquid feed tank at the respective proximal ends. However, it is preferable to use inner and outer tubes of a flexible double tube as the wash liquid conduit and the compressed air conduit, respectively. An injection fluid conduit may be extended parallel relation with the flexible double tube, but it is more desirable to turn the fluid conduit through 90 degrees toward a connection port which is provided at a lateral side of the conduit coupler member to facilitate connection and disconnection of a fluid feed tube to and from the conduit coupler member. The compressed air conduit, i.e., the outer tube of a flexible double tube, may be once connected to an air chamber which is formed internally of the coupler body of the conduit coupler member in communication with a connecting passage, which is opened in a connecting end face of the conduit coupler member. Further, preferably an on-off valve is provided at a fore distal end of the wash liquid conduit, namely, at a fore distal end of the inner tube of the flexible double tube, the on-off valve being adapted to be inserted into the wash liquid conduit as a connecting passage. Further, preferably the injection passage is provided with a pipe-like injection fluid feed conduit at a distal end, to be inserted into a connecting passage from the connection port at a lateral side of the conduit coupler member.

A fluid is supplied to the injection passage not from an injection fluid conduit which is directly connected to the multiplex connector on the universal connection cable but from an injection fluid conduit which is disconnectibly connected to a connection port at a lateral side of a coupler body of the conduit coupler member. Therefore, on the conduit connection terminal on the multiplex connector, simply coupling ends of the wash fluid conduit and the compressed air conduit are opened along with a coupling end of the injection fluid conduit to the injection passage, making it possible to simplify and compactify the construction of the connector. Besides, when the injection fluid conduit is connected the connection port on the conduit coupler member, both the observation window washer means and the fluid injection means can be connected to the endoscope by one simple action, that is, by plugging the conduit coupler member into the conduit connection terminal on the connector.

BRIEF DESCRIPTION OF THE DRAWINGS

The above and other objects, features and effects of the present invention will become apparent from the following description of a preferred embodiment, taken in conjunction with the accompanying drawings. Needless to say, the present invention is not limited to particular forms exemplified in the drawings.

In the accompanying drawings.

DESCRIPTION OF PREFERRED EMBODIMENT

Figure 1:
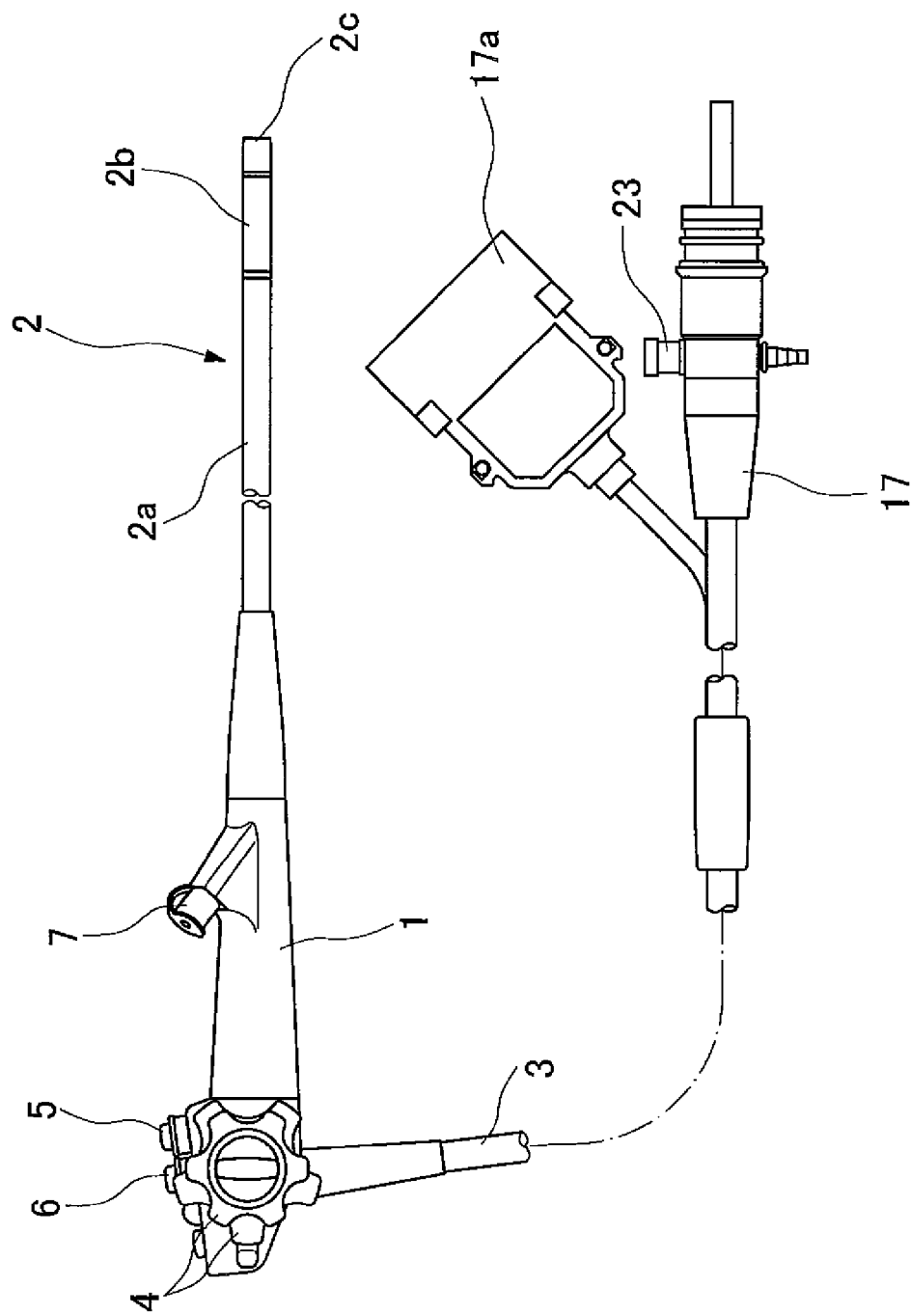
FIG. 1 is a schematic outer view of an endoscope embodying the present invention.

Now, the present invention is described more particularly by way of a preferred embodiment shown in the accompanying drawings. Shown in FIG. 1 is the general layout of an endoscope embodying the present invention. In that figure, indicated at 1 is a manipulating head assembly of the endoscope, at 2 an elongated insertion member which is extended forward from the manipulating head assembly 1 and at 3 a universal connection cable which is led out on one side of the manipulating head assembly 1. The manipulating head assembly 1 is gripped in an operator's hand to manipulate and operate the endoscope. The insertion member 2 is extended forward from the manipulating head assembly 1 for introduction into a body cavity of a patient. The universal connection cable 3 is connectible to external component units like a light source and an image processor.

An elongated flexible portion 2a, which constitutes a major part of the insertion member 2 from a proximal end which is connected to the manipulating head assembly 1, is flexible in bending directions and attached with a rigid tip end section 2c at its fore distal end through an angling section 2b. Incorporated into the manipulating head assembly 1 are mechanisms for operating the endoscope. A control knob 4 is provided at a lateral side of the manipulating head assembly 1 thereby to turn the angling section 2b of the insertion member 2. By way of this control knob 4, the angling section 2b can be angularly turned in the fashion of remote control to direct the rigid tip end section 2c toward an arbitrary direction. Further, an air/liquid feed valve 5 and a suction valve 6 are provided on the manipulating head assembly 1, in addition to an entrance 7 to a tool inserting channel.

Figure 2:
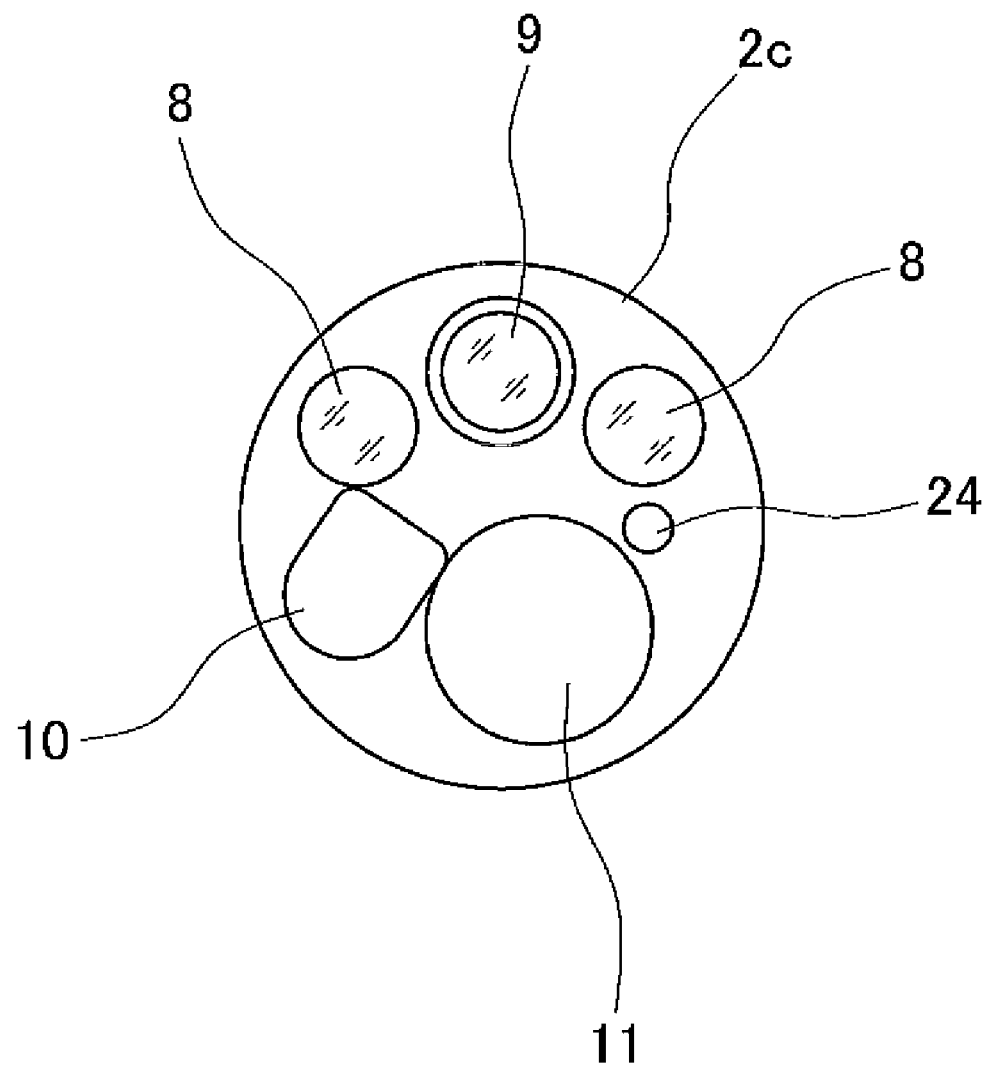
FIG. 2 is a schematic front view of a rigid tip end portion of an elongated endoscopic insertion member.

As shown in FIG. 2, illumination windows 8 and an optical observation window 9 are provided at a distal end of a casing of the rigid tip end section 2c to take images of an intracavitary portion of interest through the observation window 9 under illumination of light which is projected through the illumination windows 8. Further, an observation window washing nozzle 10 is provided on the casing of the rigid tip end section 2c, along with a tool outlet hole 11 from which a forceps or other surgical tool is protruded into a body cavity.

Figure 3:
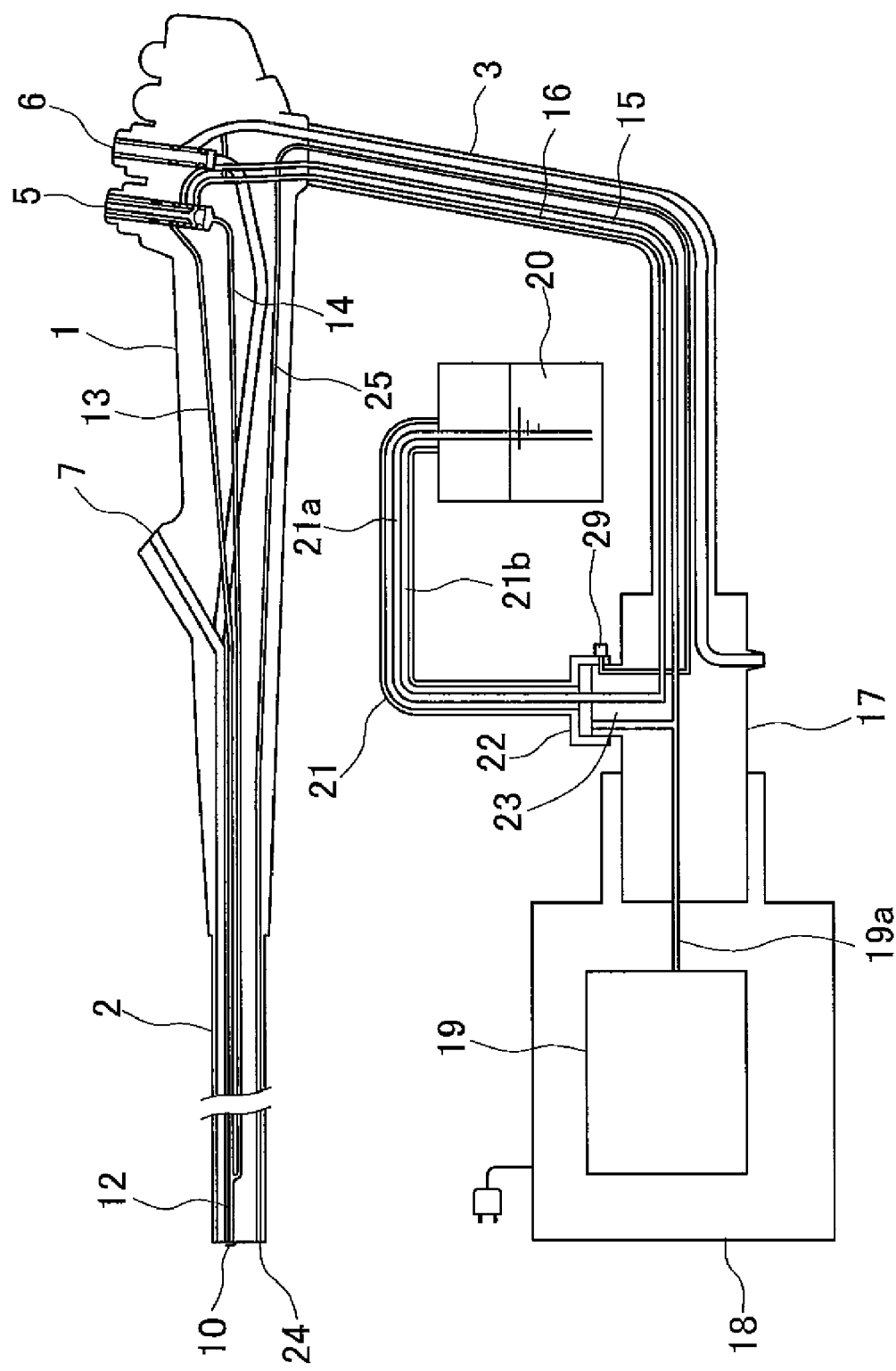
FIG. 3 is a schematic illustration of an endoscopic fluid feed system according to the present invention.

Shown schematically in FIG. 3 is an endoscopic fluid feed system according to the invention. The endoscopic fluid feed system is composed of an observation window washer means for cleaning an endoscopic observation window 9 and a fluid injection means for spurting a liquid or fluid toward a target site on an intracavitary wall.

The observation window washer means has an air/liquid passage 12 which is extended internally of the insertion member 2 as far as a nozzle 10 on the rigid tip end section 2c at the fore distal end of the insertion member 2. At a midway point, more particularly, at the angling section 2b of the insertion member 2, the air/liquid passage 12 is branched into an air passage 13 and a liquid passage 14, both of which are extended into the manipulating head assembly 1 and connected to an air/liquid feed valve 5. Further, an air feed passage 15 and a liquid feed passage 16 are connected to the air/liquid feed valve 5. Communication between the air feed passage 15 and the air passage 13 as well as communication between the liquid feed passage 16 and the liquid passage 14 is opened or closed by manually operating the air/liquid feed valve 5. Thus, a compressed air feed line is constituted by the air feed passage 15 and the air passage 13, while a wash liquid feed line is constituted by the liquid feed passage 16 and the liquid passage 14. Further, the air/liquid passage 12 serves as a common conduit for compressed air and a wash liquid, and, by way of the wash fluid feed lines just described, compressed air or a wash liquid is selectively supplied to the nozzle 10.

Both of the air feed passage 15 and liquid feed passage 16 are extended as far as connection points on a multiplex connector 17 at a distal end of a universal connection cable 3. The multiplex connector 17 is disconnectibly connectible to external component units including a light source device 18 with a source lamp within its housing. Illumination light from the source lamp is fed to the illumination windows 8 on the rigid tip end section 2c of the insertion member 2 from the light source 18 by way of a light guide which is extended as far as the rigid tip end section 2c via the multiplex connector 17, universal connection cable 3 and manipulating head assembly 1, and projected through the illumination windows 8 to illuminate an intracavitary site of interest. In addition, the multiplex connector 17 is provided with an electric connector 17a which is disconnectibly connectible, for example, to an image processor (not shown).

Figure 4:
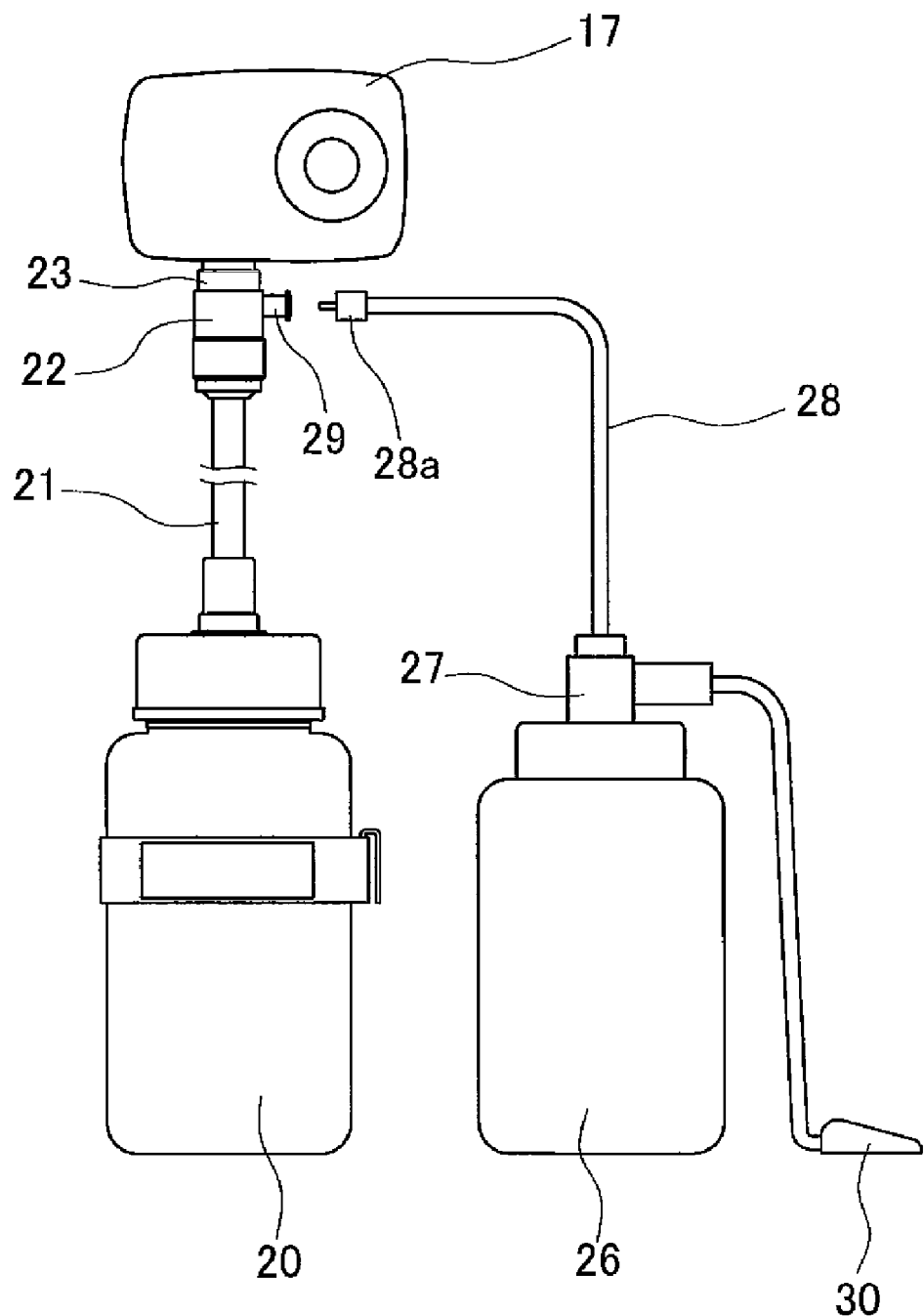
FIG. 4 is a schematic illustration of a conduit coupler member which is adapted to connect both endoscopic observation window washer and fluid injection means simultaneously to the endoscope.
Figure 5:
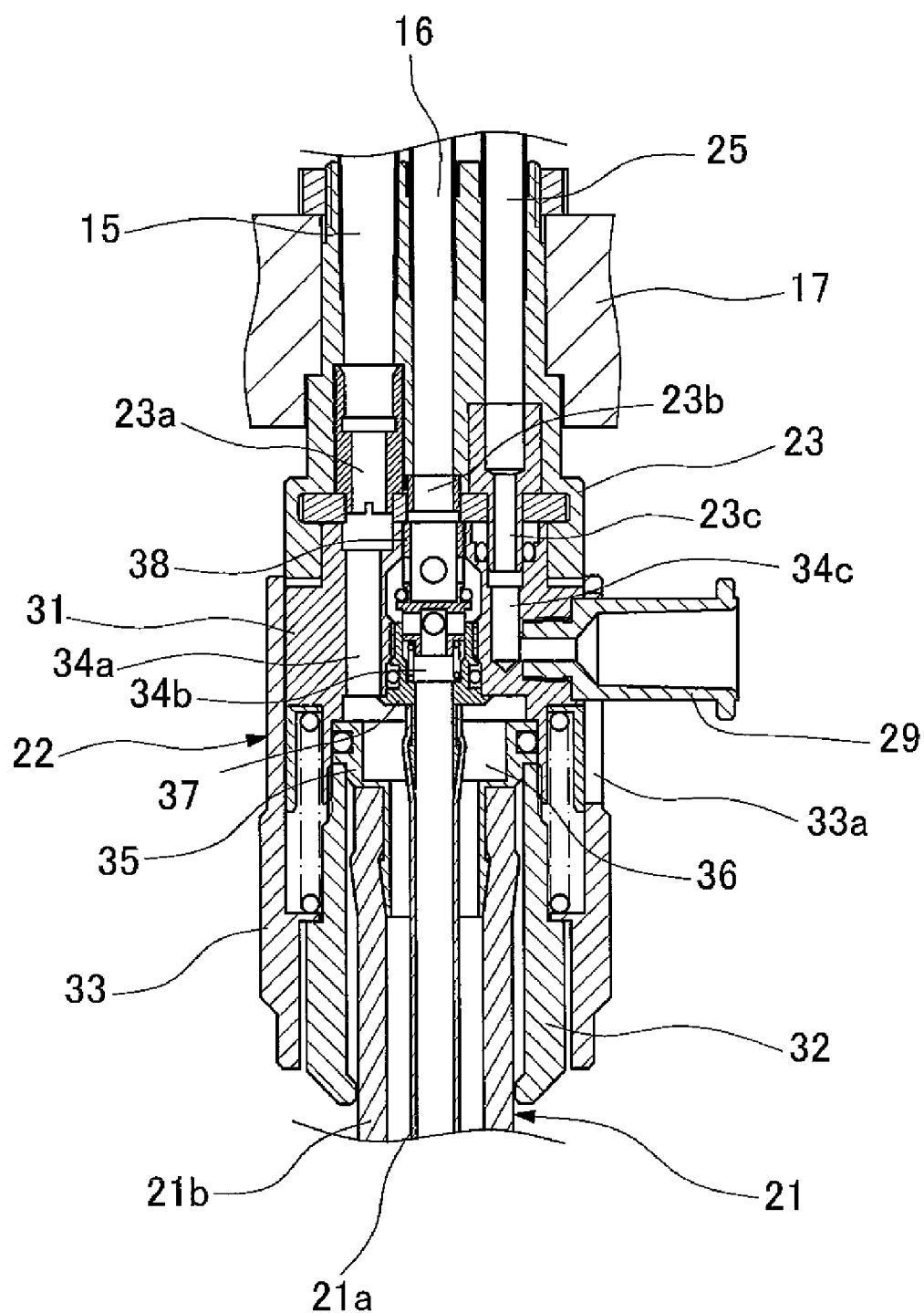
FIG. 5 is a fragmentary longitudinal section, showing the conduit coupler member of FIG. 4 on an enlarged scale.
Figure 6:
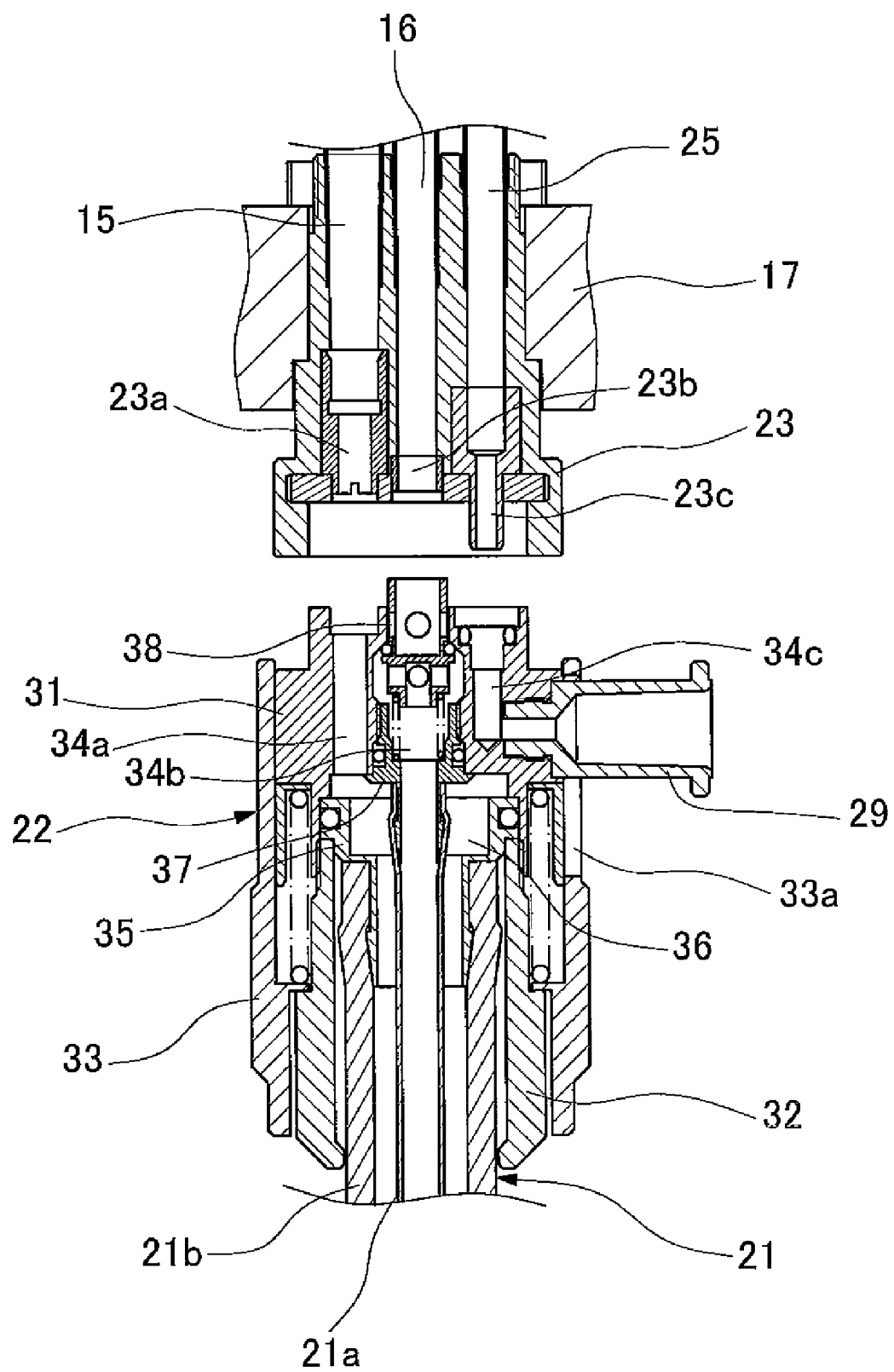
FIG. 6 is a sectional view similar to FIG. 5, showing the conduit coupler member unplugged from a conduit connection terminal on the side of a multiplex connector.

An air pump 19 is built in the light source 18 to supply compressed air to the air passage 13 of the observation window washer means. The liquid passage 14 receives a supply of a wash liquid from a liquid feed tank 20 which is located outside the light source 18. Normally, the liquid feed tank 20 is fixedly retained on the light source 18, and a wash liquid is supplied from the liquid feed tank 20 by applying a pressure on a wash liquid surface in the liquid feed tank 20, with compressed air which is supplied from the air pump 19 through an air pipe 19a. As shown in FIGS. 4 through 6, a flexible double tube 21 is connected to the liquid feed tank 20 to serve as a wash liquid tube and a compressed air tube. More particularly, in the case of the particular embodiment shown, an inner tube 21a of the flexible double tube 21 is used as a wash liquid conduit tube while an outer tube 21b is used as a compressed air conduit tube 21b. Attached to a fore distal end of the flexible double tube 21 is a conduit coupler member 22 which is disconnectibly connectible with a conduit connection terminal 23 on the part of the multiplex connector 17.

As shown in FIG. 2, the fluid injection means has a fluid injection hole 24 opened in a distal end face of the rigid tip end section 2c. As seen in FIG. 3, a fluid injection passage 25 is led to the fluid injection hole 24. This injection passage 25 is extended internally through the insertion member 2 and through the universal connection cable 3 via the manipulating head assembly 1.

In this instance, the fluid injection means is provided for injection of a wash fluid, a medicinal liquid or a coloring agent into a body cavity, and, as seen in FIG. 4, includes a fluid storage tank 26 holding a fluid to be injected toward an intracavitary site under observation. A fluid feed pump 27 is mounted on the tank 26, and a flexible fluid feed tube 28 is connected to a discharge side of the fluid feed pump 27. A coupling member 28a which is provided at the distal end of the fluid feed tube 28 is disconnectibly connected to a connection port on the part of the conduit coupler member 22. The fluid feed pump 27 is turned on and off by way of a foot switch 30. In this case, upon stepping on the foot switch 30, the pump 27 is activated to pump out an injection fluid from the storage tank 26. Upon removing a foot from the foot switch 30, the pump 27 is deactivated to suspend delivery of an injection fluid.

Further, as seen in FIGS. 5 and 6, three through passages are provided axially and internally of the multiplex connector 17. Namely, provided internally of the multiplex connector 17 are three through passages including a compressed air conduit 23a in communication with the air supply conduit 15, a wash fluid conduit 23b in communication with the liquid supply conduit 16, and an injection fluid conduit 23c in communication with the injection passage 25. Each one of the just-mentioned conduits 23a to 23c is opened in a coupling face of the conduit connection terminal 23. As the conduit coupler member 22 is connected to the conduit connection terminal 23, the compressed air conduit 23a of the air feed passage 15 is brought into communication with the compressed air conduit 21b, and the wash fluid conduit 23b of the liquid feed passage 16 is brought into communication with the wash fluid feed conduit 21a. Further, the injection fluid feed conduit 28 is brought into communication with the injection fluid conduit 23c of the injection passage 25 through the connection port 29.

The conduit coupler member 22 at the distal end of the flexible double tube 22 is composed of a coupler body proper 31, and a retainer ring 32 which is threaded into the conduit coupler 22. Further, the conduit coupler member 22 is provided with an outer ring 33 which is fitted in such a way as to enshroud the coupler body proper 31 and the retainer ring 32. Provided internally of the coupler body 31 are first to third connection passages to be brought into communication with the conduits 23a to 23c on the part of the conduit connection terminal 23 on the multiplex connector when the conduit coupler 22 is plugged into the connection terminal 23.

Gripped between the coupler body 31 proper and retainer ring 32 is a first conduit connecting member 35 to be connected to the distal end of the compressed air conduit 21b, i.e., the outer tube of the flexible double tube 21. The compressed air conduit 21a which is connected to the first conduit connecting member 35 is opened to an air chamber 36, which is in communication with a first connecting passage 34a. The wash liquid feed tube 21a, i.e., the inner tube of the flexible double tube 21, is extended through the air chamber 36 and attached to a second conduit connecting member 37 which is fitted in a second connecting passage 34b. An on-off valve 38 is provided at a position forward of the second conduit connecting member 37 of the second connecting passage 34b. This on-off valve 38 is adapted to close the second connecting passage 34b when the conduit coupler member 22 is disconnected from the conduit connection terminal 23.

Upon plugging the conduit coupler 22 into the conduit connection terminal 23, the first connecting passage 34a is brought into communication with the compressed air conduit 23a, and a fore end portion of the on-off valve 38 of the second connecting passage 34 is inserted into the wash liquid conduit 23b and as a result the on-off valve 38 is slid along the second connecting passage 34b and opened to bring the second connecting passage 34b into communication with the wash liquid conduit 23b. At the same time, the injection fluid conduit 34c of a pipe-like form is inserted into and brought into communication with the third connecting passage 34c which is bent at right angles within the coupler body proper 31. The third connecting passage 34c is in communication with a connection port 29 which is threaded into a lateral side of the outer ring 33. The coupler body 31 is enshrouded in the outer ring 33, and the connection port 29 is fitted in the third connecting passage 34c through a slot 33a which is formed in the outer ring 33.

With the endoscopic fluid feed system as described above, the injection fluid feed tube 28 is connected to the connection port 29 prior to use. What is required on starting an endoscopic examination is simply to plug the conduit coupler member 22 in the conduit connection terminal 23 on the multiplex connector 17. By this simple plug-in action, the observation window washer means as well as the fluid injection means is connected to the endoscope. That is, the compressed air conduit 21b and the wash liquid conduit 21a are connected with the air feed passage 15 and the liquid feed passage 16, respectively. Thus, by manipulating the air/liquid feed valve 5, a wash liquid is sent to the nozzle 10 and spurted toward the observation window 9 to wash away deposited contaminants therefrom. In the next place, in place of a wash liquid, air is blasted against the observation window 9 to purge droplets of the wash liquid therefrom.

In case an intracavitary wall site under observation is covered with contaminants, the pump 27 is activated by stepping on the foot switch 30, whereupon a liquid such as a physiological saline solution in the liquid storage tank 26, for example, is supplied to the third connecting passage 34c from the injection fluid feed conduit 28 via the connection port 29. This third connecting passage 34c is communicated with the injection fluid conduit 23c on the conduit connection terminal 23, so that a fluid from the fluid storage tank 26 is fed to the injection passage 25 from the injection fluid conduit 23c and spurted out through the injection hole 24 on the rigid tip end section 2c to wash away contaminants from the intracavitary wall site under observation. Otherwise, in case a coloring agent is stored in the tank 26, it is sprinkled over an intracavitary wall site under observation.

As described above, since the injection fluid feed conduit 28 from the fluid storage tank 26 is connected to the conduit coupler member 22 at the distal end of the flexible double tube 21 of the observation window washer means, which is connectible to the conduit connection terminal 23 on the multiplex connector 17, it suffices for the connector 17 to have only three conduits 23a to 23c. That is to say, the multiplex connector 17 can be provided in a compact form, simplified in construction. Thus, at the time of using the endoscope, the observation window washer means and the fluid injection means can be connected to the endoscope simply by plugging the conduit coupler member 22 into the conduit connection terminal 23, and the observation window washer means as well as the fluid injection means can be disconnected from the endoscope simply by unplugging the conduit coupler member 22 from the conduit connection terminal 23.

What is claimed is:

1. An endoscopic fluid feed system for use with an endoscope having an endoscopic optical observation window on a rigid tip end portion at a fore distal end of an elongated insertion member extended forward from a manipulating head assembly, a multiplex connector provided at a proximal end of a universal connection cable to disconnectibly connect said endoscope to external component units, and an observation window washer means and a fluid injection means for injecting a fluid into a body cavity from an injection passage leading to an injection hole opened on said rigid tip end portion of said insertion member, characterized in that said fluid feed system comprises:
    a conduit connection terminal provided on said multiplex connector, providing connection ports for a wash fluid conduit and a compressed air conduit of said observation window washer means; and
    a conduit coupler member adapted to be disconnectibly connected to said conduit connection terminal and internally formed with a wash liquid supply conduit in communication with a liquid feed tank, and a compressed air supply conduit to be disconnectibly connected to said compressed air conduit for supply of compressed air to apply a pressure on a liquid surface in said liquid feed tank;
    an air chamber formed between said conduit coupler member and said conduit connection terminal when connected so as to communicate said compressed air conduit to said compressed air supply conduit;
    a normally closed on-off valve provided in said wash fluid conduit adapted to bring, into communication with said wash liquid supply conduit when said conduit coupler member being connected to said conduit connection terminal;

said conduit coupler member being provided with an injection fluid connection port to said injection passage, which injection fluid connection port being disconnectibly connectible to an injection fluid supply conduit;

said injection fluid connection port being communicated with said injection fluid passage when said conduit coupler member is connected to said conduit connection terminal.

2. An endoscopic fluid feed system as set forth in claim 1, wherein connection ports to said wash liquid conduit and said compressed air conduit are opened on said conduit connection terminal along with a connection port to said injection passage, while said conduit coupler member having first to third connection ports opened on an end face of a coupler body, said first to third connection ports being connectible to said wash liquid conduit, compressed air conduit and injection passage, said coupler body being adapted to be disconnectibly connected to said conduit connection terminal.

3. An endoscopic fluid feed system as set forth in claim 1, wherein said wash liquid supply conduit and said compressed air supply conduit of said conduit coupler member are constituted by inner and outer tubes of a flexible double tube, a coupler body having first and second connecting passages opened in a coupling end face for circulation of compressed air in supply from said compressed air supply conduit via an air chamber and an injection fluid in supply from said connection port.

4. An endoscopic fluid feed system as set forth in claim 3, wherein said connection port is provided at a lateral side of said conduit coupler member in communication with a third connecting passage being bent at right angles toward a coupling end face of said coupler body.

5. An endoscopic fluid feed system as set forth in claim 4, further comprising an on-off valve provided in said second connecting passage and adapted to be pushed into said wash liquid feed conduit, while said third connecting passage is adapted to receive an injection fluid conduit on the side of said injection passage.

\* \* \* \* \*